United States Patent [19]

Knutson

[11] 4,401,651

[45] Aug. 30, 1983

[54] WOUND-HEALING COMPOSITIONS CONTAINING POVIDONE-IODINE

[76] Inventor: Richard A. Knutson, 130 N. Shelby St., Greenville, Miss. 38701

[21] Appl. No.: 171,261

[22] Filed: Jul. 22, 1980

Related U.S. Application Data

[63] Continuation-in-part of Ser. No. 31,162, Apr. 18, 1979, abandoned.

[51] Int. Cl.³ .................. A61K 31/79; A61K 33/18
[52] U.S. Cl. .................... 424/80; 424/150; 424/180
[58] Field of Search ............ 424/80, 150, 180

[56] References Cited

U.S. PATENT DOCUMENTS

| | | | |
|---|---|---|---|
| 434,727 | 8/1890 | Schmidt | 424/180 X |
| 1,611,962 | 12/1926 | Toloner | 424/180 X |
| 1,812,238 | 6/1931 | Hammer | 424/150 |
| 2,826,532 | 3/1958 | Hosmer | 424/150 X |
| 4,094,967 | 6/1978 | Gilbert | 424/28 |

FOREIGN PATENT DOCUMENTS

| | | |
|---|---|---|
| 294734 | 8/1928 | United Kingdom . |
| 673578 | 6/1952 | United Kingdom . |
| 760579 | 11/1956 | United Kingdom . |
| 1458430 | 12/1976 | United Kingdom . |

OTHER PUBLICATIONS

Martindale–"The Extra Pharmacopoeia"–27th Ed., p. 65, 1977.
"The Pharmaceutical Codex" 11th Ed., pp. 612–614, 900–901 (1979).
Vanderwyk–"Medical & Surgical Antisepsis with Betadine Microbicides"; pp. 17–25, Pub. Purdue Frederick Co. (1972).
Dineen–"Medical & Surgical Antisepsis with Betadine Microbicides", pp. 88–90 & 98–111, Pub. Purdue Frederick Co. 1972.
Handbook of Non Prescription Drugs, 5th Ed., 1977, pp. 313–315 & 356–359.
Polk–"Medical & Surgical Antisepsis with Betadine Microbicides", pp. 91–94–Pub. Purdue Frederick Co. (1972).
Bernard–"Medical & Surgical Antisepsis with Betadine Microbicides", pp. 95–97, Pub. Purdue Frederick Co. (1972).
Dineen–"The World Congress on Antisepsis", pp. 44–47, Pub. H. P. Publishing Co. (1978).
Bohmert–"The World Congress on Antisepsis" pp. 103 & 104, Pub. H. P. Publishing Co. (1978).
Helm–"The World Congress on Antisepsis" pp. 105–108, Pub. H. P. Publishing Co. (1978).
The Merck Index, 9th Ed., 1976, pp. 996–997, Items 7498 & 7499.
Chem. Abstr., 50, 11623g (Shelanski, USP 2,739,922, 3/27/56).
Chem. Abstr., 50, 15908a [Shelanski, *J. Intern. Coll. Surgeons*, 25, 727–734 (1956)].

*Primary Examiner*—Leonard Schenkman
*Attorney, Agent, or Firm*—Berman, Aisenberg & Platt

[57] ABSTRACT

Admixtures of (a) an antifungal/antibacterial agent, such as povidone-iodine, (b) sugar and (c) suitable carrier are substantially non-allergenic, have excellent healing properties when applied to burns or open wounds and serve as an effective barrier to the growth of healing tissue into gauze or similar dressing.

1 Claim, No Drawings

WOUND-HEALING COMPOSITIONS CONTAINING POVIDONE-IODINE

RELATED APPLICATION

This application is a continuation-in-part of co-pending application Ser. No. 31,162, (now abandoned) filed Apr. 18, 1979, the entire disclosure of which is incorporated herein by reference.

TECHNICAL FIELD

Dressings are regularly used to cover open wounds and burns. There is an ever-present need for non-allergenic antibacterial and antifungal compositions which have superior healing properties and permit the covering of such wounds or burns without having healing tissue grow into gauze or similar material.

BACKGROUND ART

For more than two years prior to the subject invention free sugar had been used on wounds either as a single constituent or in conjunction with povidone-iodine (Betadine ® solution). During this period sugar was poured directly into the wound (if the wound was deep), a 4-inch (10.16 centimeters) by 4-inch sponge or other dressing material was soaked in Betadine ® solution and used to dress the wound and the dressing was changed at intervals of from 6 to 8 hours; shallow wounds were dressed with Betadine ® solution-soaked sponges which were then coated with approximately 0.25 inch (0.635 centimeter) of sugar and applied face down (sugar in direct contact with the wound) to the wound.

Notwithstanding handling difficulties and lack of control or uniformity, wound-healing time was markedly reduced in this manner. In more than 300 cases such use of povidone-iodine solution in conjunction with sugar proved to be a safe, reliable and rapid method for healing of a variety of wounds. These wounds included both clean and infected, fresh and old wounds. Their variety extended from simple abrasions and lacerations to massive soft tissue trauma, including burns, crush injuries, shot-gun and gun shot wounds; decubitus, diabetic and stasis ulcers; and exposed, fractured bone.

In massive soft tissue injuries (such as shot-gun wounds and second- or third-degree burns) debridement was essential as in routine wound care. Thereafter, repeated dressing changes with sugar and povidone-iodine solution were found to produce a clean, granulating wound in rapid fashion, with no production of eschar and no superficial infection, despite the absence of systemic antibiotics.

Surprisingly, this treatment produced large amounts of granulation tissue in quantities sufficient to fill in large soft-tissue defects secondary to the original wound. Skin rather rapidly covered the new, exuberant granulation tissue spontaneously, thereby largely reducing healing time and the necessity for skin grafting.

Regeneration of tissue, rather than retraction of the wound, was the general rule. In many cases the healed wound was soft and resilient, with good sensation.

There is good evidence to suggest that sugar products, such as honey and molasses, were used in treating wounds, including burns, in ancient times. Evidence suggests that the native American Indians from Canada to the Inca Empire were adept in the use of a number of medicinal compounds which showed considerable promise in the treatment of wounds and burns. These included herbs, root extracts, leaf extracts and varieties of maple syrup, sorghum, molasses, honey and eventually sugar (as sugar cane). In ancient Egypt, preservation of food and treatment of wounds included the use of sugar products.

Povidone-iodine (polyvinylpyrrolidone-iodine complex) is a topical anti-infective ("The Merck Index", ninth edition, pages 996 and 997, entry 7499, Merck & Co., Inc., 1976) which is commercially available in a number of forms, e.g., Betadine ® antiseptic gauze pad, solution, solution swab aid, aerosol spray, surgical scrub, douche, vaginal gel, skin cleanser, ointment, microbicidal bath, perineal wash and whirlpool concentrate [Physicians' Desk Reference" (PDR), 31st edition, pages 1263 to 1265, 1977].

Typical formulations for PVP-I products, such as Betadine ® solution (1000 liters) and Betadine ® ointment (one pound), are:

| PVP-I Solution | |
|---|---|
| (a) PVP-I Powder | 125 kg |
| (b) Sodium Phosphate (tribasic) | 7.5 kg |
| (c) Triton X-114 | 4.0 kg |
| (d) Water (q.s.) | 1000 liters |
| (Triton X is polyethylene glycol p-isooctylphenyl ether) | |
| Analysis | |
| (a) pH: | Less than 6.0 |
| (b) Density: | 1.03 to 1.04 |
| (c) Viscosity: | 15 to 25 cp |
| (d) Superficial Tension: | 31 to 33 dynes/cm |
| (e) Available Iodine: | 1.15–1.20% |
| PVP-I Ointment | |
| (a) PVP-I Powder | 45.5 g |
| (b) PEG 400 (Carbowax) | 272.4 g |
| (c) PEG 4000 (Carbowax) | 113.5 g |
| (d) Water (q.s. one pound) | 22.7 g |
| Analysis | |
| (a) Viscosity at 70° C. | 18,000 to 22,000 cp |
| (b) Available Iodine | 1.05 to 1.13% |

INVENTION

An admixture (hereafter: the subject composition) of (a) an antifungal/antibacterial agent, such as povidone-iodine, (b) an antibacterial tissue nourisher, e.g. sugar (which is, per se, a strong antibacterial agent in high concentrations and functions as a stimulant to the growth of granulation tissue) and (c) a suitable carrier, in appropriate proportions, provides a stable effective antibiotic composition which facilitates healing of wounds to which it is directly applied, prevents growth of granular tissue into covering dressing and otherwise satisfies the hereinafter-recited objectives.

The antifungal/antibacterial agent is any such agent which is compatible with sugar. It is advantageously water soluble for ease of handling and for removal from tissue being treated. It is preferably non-allergenic so that it might have a wider scope of applicability. Povidone-iodine satisfies all of these criteria, is the antifungal/antibacterial agent of choice and is thus used throughout the disclosure in provided examples. Any other antifungal/antibacterial agent that is compatible with sugar and is therapeutically acceptable for administration directly to open wounds is alternatively combined with a sugar, e.g. sucrose, dextrose, maltose, fructose, honey and molasses, in the same or comparable manner.

Povidone-iodine (PVP-I) is conveniently provided in the form of Betadine ® ointment (10 percent povidone-iodine) and Betadine ® solution (10 percent povidone-iodine), since these are in suitable carrier and no further carrier is required. Alternatively, the antifungal/antibacterial agent is separately combined with sugar, any (preferably) water-soluble and substantially-inert physiologically-acceptable ointment base, e.g. Unibase ®, and, optionally, water (to make more fluid) or, e.g., carboxymethylcellulose (to make less fluid) to obtain an appropriate consistency and stability. Naturally, other ointment bases, such as petroleum jelly, are similarly useful if water-solubility is not required.

The sugar is suitably in the form purchased at any grocery store; it need not be specially purified, sterilized or otherwise treated. Although sucrose is preferred in view of its low cost and availability, such can be partially or wholly replaced by dextrose, maltose, fructose, honey, molasses or similar high-sugar-content substance. All references herein to sugar optionally include (individually or in any combination) each of the preceding; all examples, however, are based on common, ordinary granulated sugar.

The ratio of sugar to, e.g., povidone-iodine, is significant from the viewpoint of cost, ease of handling and effectiveness. When the povidone-iodine is in the form of Betadine ® ointment and Betadine ® solution, the weight ratio of sugar to Betadine ® ointment acceptably varies from 1:1 to 8:1, with the amount of Betadine ® solution gradually increasing from zero for the 1:1 ratio to 0.5 ounce per pound (0.03125 gram per gram) for the 2.5:1 ratio to 1 ounce per pound for the 4:1 ratio to 2 ounces per pound for the 8:1 ratio (based on the total weight of sugar and Betadine ® ointment).

For extended shelf life, the range is advantageously limited to 2.5:1 to 5:1. Below that range (from 1:1 to 2.5:1) the components tend to separate but are readily redispersed by stirring shortly before use; above that range (from 5:1 to 8:1) the components tend to separate and crystallization occurs.

The preferred formulation is that based on 20 parts by weight of sugar (sucrose), 5 parts by weight of Betadine ® ointment and 2 parts by weight of Betadine ® solution. This corresponds to 100 parts by weight of sugar, 3.5 parts by weight of povidone-iodine and 31.5 parts by weight of carrier. When the components are mixed in these proportions, the resulting admixture holds together and maintains its consistency in both heat and cold for long shelf life; it is easy to apply and has high patient acceptance. In addition, these amounts have been arrived at through experimentation with various proportions of the respective components; these proportions have been found to be the most useful, not only for the compounding of this mixture, but for the efficacy of the product in terms of various wounds and treatments for which it has been employed. That is to say, a proportion of sugar approximating 70 to 80 percent by weight (based on total composition weight) appears to be the optimum for wound healing. This corresponds closely with the concentration of sugars in honey.

OBJECTIVES

1. To provide a composition which inhibits the growth and proliferation of and kills bacteria and fungi which it contacts.

2. To provide a microbicidal and antibiotic composition which will, when employed as a wound dressing, result in a clean debrided wound.

3. To provide a composition having a consistency which facilitates its use directly on and in conjunction with the dressing of open wounds and burns.

4. To provide a composition which is stable (shelf-life and temperature) against separation or crystallization or is at least susceptible to controlled application, e.g., by stirring shortly before use.

5. To provide a composition which cleans tissue it contacts so that the tissue can present a bed for forming granulation tissue.

6. To provide a composition which encourages formation of exuberant granulation tissue in a clean environment.

7. To provide a composition which encourages epithelialization from the edges of a wound while granulation tissue fills the defect without eschar.

8. To provide a composition which enables a wound to be covered by skin with little or no defect.

9. To provide a single composition which serves as (a) an antibiotic and antifungal agent, (b) food and nourishment for granulation tissue and (c) encouragement for skin coverage.

10. To provide a composition which serves as a topical anesthetic, reducing the need for narcotics.

11. To provide a composition which reduces or eliminates growth of wound tissue (to which it is applied) into gauze or similar covering material.

12. To provide a composition which encourages tissue regeneration.

13. To provide a water-soluble and water-washable antimicrobial product which has a smooth to slightly granular texture, is directly applicable to wounds and burns, facilitates rapid healing with minimal scarring, readily adheres to dressings and prevents growth of granular tissue into the dressing.

14. To provide an economical composition which is effective in treating a full spectrum of wounds incurred by man and other animals.

15. To provide a unitary composition which is portable as such and need not be applied as separate components to a wound or to dressing material.

16. To provide a medicament composition which is directly applicable to a wounded tissue and is stable thereon when so applied.

17. To provide a medicament composition which is easy to apply either directly to wounded tissue or to a dressing material without spillage or creating any mess.

18. To provide a medicament composition which is substantially uniform and consistent throughout and which is thus administrable by a readily-followed specified technique which leads to predictable results.

19. To provide a substantially non-drying medicament composition which does not harden and adhere strongly to wounded tissue to which it is applied.

20. To provide a medicament composition with a consistency which makes it easy to handle; it neither crumbles (flakes off) nor flows, but it does hold together.

21. To provide a substantially homogeneous composition for treating burns and open wounds and which has a high degree of patient acceptability.

22. To provide a medicament composition which stays in place when applied directly to wounded tissue and is readily removable at a later time without injuring such tissue.

23. To provide an open-wound-treating composition which maintains long-lasting cleansing and healing properties in situ and thus minimizes the frequency of needed dressing changes.

24. To provide a smooth and soothing medicament composition with minimal, if any, irritation to wounded tissue to which it is applied.

25. To provide a medicament composition which permits complete and uniform coverage of wounded tissue.

26. To provide a composition which imparts a cooling sensation to and an anesthetic effect on wounded tissue to which it is applied.

27. To provide a composition which enables the placement of uniform and controlled amounts of a sugar substance and of an antifungal/antibacterial in direct contact with wounded tissue; the contact is predictable and constant with regard to both of these components.

28. To provide a wound-healing composition which promotes the formation of healing tissue as firm granulation tissue which continues to build up and to become the surface tissue as the wound heals.

29. To provide a wound-treating composition which is an improved debrider and reduces eschar formation.

30. To provide a wound-treating composition which is easily applied by patients with minimal instruction.

31. To provide a composition with which patients are willing to redress wounds as required.

32. To provide a wound-treating composition which renders wounds substantially odorless.

33. To provide a wound-treating composition which is readily and effectively applied without need for observing "sterile" conditions, thus materially reducing the cost of dressing and associated materials and the time required to apply and to change dressings.

COMPONENTS OR INGREDIENTS

Although repeated reference is made to sugar or sucrose, to povidone-iodine and to carrier used in Betadine ® ointment and in Betadine ® solution, these are merely illustrative of preferred embodiments; the subject invention is not so limited.

In lieu of sucrose, any strong antibacterial (in high concentration) agent which functions as a stimulant to the growth of granulation tissue, including other sugars and sugar-providing components (such as fructose, glucose, dextrose, maltose, maple syrup, brown sugar, sorghum, honey and molasses), aloe, zinc oxide, kerosene, tar oil or any combination thereof, is suitable. Ordinary table sugar is preferred in view of its availability and cost. When honey, molasses or similarly-fluid material is employed in place of sugar, the amount of separate carrier is optionally reduced or even eliminated. This component is referred to, generically, merely as "sugar" throughout most of this text.

Likewise, the subject compositions are not limited to those wherein povidone-iodine is the antifungal/antibacterial component. Such component is replaced wholly or partially by one or more different ingredients with similar and/or related properties. The ingredient is, optionally, insoluble or merely dispersible in water, but is preferably water soluble; it may be, but is preferably not, an antibiotic; ideally, it is not allergenic. Illustrative of the ingredients which comprise this component, in whole or in part, are:

| | | |
|---|---|---|
| acrisorcin | gentian violet | nitrofurazone |
| Amphotericin B | Griseofulvin | Nystatin |
| anthralin | haloprogin | povidone-iodine |
| Candicidin | hexachlorophene | resorcinol |
| dibromopropamidine isethionate | ichthammol | sulfabromomethazine |
| domiphen bromide | iodochlor-hydroxyquin | undecylenic acid |
| fluorouracil | iodoform | zinc undecylenate |

In order to provide the combination of the "sugar" and the antifungal/antibacterial component with the desired consistency, one or a combination of carriers is ordinarily required. Ingredients from which the carrier is formulated in any suitable combination include, e.g.:

| | |
|---|---|
| agar | PEG 4000 |
| cold cream | PEG 6000 |
| corn oil | povidone |
| cottonseed oil | propylene glycol |
| gelatin | silica gel |
| glycerin | sodium alginate |
| hydrophilic ointment | sodium carboxymethylcellulose |
| hydrophilic petrolatum | sorbitol solution |
| lanolin | spermaceti |
| methylcellulose | starch |
| olive oil | stearic acid |
| peanut oil | stearyl alcohol |
| pectin | water |
| polyethylene glycol (PEG) 400 | white ointment |
| PEG 600 | white petrolatum |
| PEG 1500 | yellow ointment |

These are standard and recognized ingredients regularly used in the formulation of topical ointments and salves. They are used in the normal fashion and are admixed with the "sugar" component to obtain a composition which does not flow, but has the desired spreadable consistency and sufficient adherence to hold it together. The composition advantageously does not comprise one or more volatile components, the loss of which (e.g. on leaving a jar of the composition uncovered) would lead to a change in the consistency of such composition.

The antifungal/antibacterial component must necessarily be physically, chemically and pharmacologically compatible with the "sugar" or sugar-providing component. When a separate carrier component is used, it must also be physically, chemically and pharmacologically compatible with both of the previously-noted essential components.

The product aspect of the invention is thus a spreadable, adherent, cohesive, substantially-homogeneous therapeutically-acceptable antimicrobial admixture of:
 (a) from 10 to 80 parts by weight of an antimicrobial tissue nourisher,
 (b) 1 part by weight of effective antifungal/antibacterial agent means which is physically, chemically and pharmacologically compatible with (a), and
 (c) carrier means to impart to the admixture a consistency which readily permits it to be spread on and to adhere to a sponge or gauze dressing and to remain in place when applied directly to tissue of an open wound or of a burn, the carrier means being physically, chemically and pharmacologically compatible with both (a) and (b) and comprising at most one third of the weight of said admixture.

Honey is suitable as (a) and/or (c).

DETAILS

The compositions of this invention provide a significant improvement over prior administration of sugar and Betadine ® solution, not only in terms of patient acceptability and ease of application to various wounds, but also in terms of the function of the product itself. Prior to the introduction of the compounded mixture, it was noted that wounded tissue would grow so rapidly that it would have a tendency to adhere to the dressing material and, therefore, wound healing was disturbed when the dressing was changed. By using povidone-iodine ointment in admixture with sugar, this problem was eliminated. The careful admixture of the various components was worked out over a period of time in order to achieve the present formulation, which has been found, on repeated testing, to be extremely efficacious and safe. It has been successfully used in a variety of treatment regimens, both operative and non-operative, and in a variety of wound situations in the office, in physical therapy and in the hospital setting. In many cases it has been found to be totally effective in the healing of a variety of wounds without the use of further surgery, skin grafting or ancillary antibiotics.

A particular problem encountered with the prior treatment regimen (sugar in conjunction with Betadine ® solution), more frequently in treating finger-tip amputations than in treating deep wounds, involved the healing of fingertip wounds at such a rapid rate that granulation tissue tended to invade the dressing material. This posed some considerable difficulty in removing the dressing and, often, a considerable amount of pain for the patient. Although tightly-woven silk or nylon dressings would prevent this problem, they also tended to limit the extent of granulation tissue expansion and thereby tended to prevent the resulting healed wound from restoration to the preinjured state.

The admixture of sugar with povidone-iodine ointment not only provided improvement by minimizing tissue growth into dressing material while retaining the positive properties of sugar and Betadine ® solution, it was also easier to apply and uniform in consistency. The separate components were subject to various techniques of administration. Spillage of Betadine ® solution and free sugar occurred during application, making a general mess. After application the separate components tended to dry out; the sugar crystallized and tended to escape from or through the dressing.

Numerous attempts were made to formulate a concoction of sugar with povidone-iodine that would adhere to a bandage and would not flow from tissue or through dressings to which it was applied, that was not generally sloppy to handle and did not result in a sticky, syrup-filled dressing. Any admixture tended to reduce the amount of sugar placed in direct contact with the wound. Premixed combinations of sugar with povidone-iodine solutions separated after standing for even a short period of time; the sugar settling at the bottom and a syrup of povidone-iodine solution and sugar layering at the top. Even using povidone-iodine ointment, compositions having at least 50 percent by weight of ointment separated and were rather gooey, whereas a composition having in excess of 80 percent by weight of sugar tended to become granular and non-adherent to itself; it was difficult to apply or to keep adhered to a dressing. A sugar:povidone-iodine ratio of 3.5:0.1 to 4:0.1 proved best with the povidone-iodine in the form of a 10 percent (by weight) ointment. This range combines optimum wound healing with both safety and economy.

The preceding ranges and proportions are predicated on the admixture of sugar with different combinations of Betadine ® ointment and Betadine ® solution, since these povidone-iodine products are readily available. When the specific composition prepared with 20 parts by weight of sugar, 5 parts by weight of Betadine ® ointment and 2 parts by weight of Betadine ® solution is admixed so that it is substantially uniform, it is extremely effective, is economical and is both shelf-life and temperature stable. The resulting proportion (20:0.7) of sugar to povidone-iodine is truly limited only by the actual nature (consistency) of the carriers used for Betadine ® ointment and Betadine ® solution. Other carriers (used singly or in appropriate combinations) produce comparably-stable admixtures having sugar/povidone-iodine weight ratios from 10:1 to 80:1 or, preferably, from 25:1 to 55:1. As povidone-iodine is water soluble, water-soluble carriers are clearly preferred, but not essential. The key is the consistency of the sugar/carrier admixture. When such consistency approximates that of the noted substantially uniform specific composition, a suitable amount of povidone-iodine is incorporated therein to produce a homogeneous admixture having the desired weight ratio of sugar to povidone-iodine. A carrier is selected so that sugar constitutes two thirds or more of the sugar/povidone-iodine final product (including carrier) in order to provide a desired sugar concentration in direct contact with tissue to which the medication is applied. By selecting water-soluble carriers with different consistencies, varying concentrations of sugar are incorporated therein to obtain stable sugar/carrier admixtures. The addition of contemplated amounts of povidone-iodine to a stable sugar/carrier admixture does not materially affect either the consistency or the stability of the admixture.

Suitable pharmacologically-acceptable water-soluble carriers are known, and their particular selection or combination is not the essence of the subject invention. The same carriers that are used in Betadine ® ointment and Betadine ® solution are optionally used with greater or lesser concentrations of povidone-iodine. Were the povidone-iodine concentration increased to 20 weight percent in each, the resulting composition (corresponding to the noted specific composition) would have a sugar/povidone-iodine weight ratio of 20:1.4; were it reduced to 5 weight percent in each, the resulting composition would have a sugar/povidone-iodine weight ratio of 20:0.35.

For any sugar/carrier admixture that is too fluid, a small proportion of a suitable stiffening agent, such as carboxymethylcellulose, is suitably added. Agents of this type also add to the stability of the admixture.

Although a stable homogeneous admixture is preferred and is herein taught, less-stable admixtures provide many of the same advantages and most of the same therapeutic properties so long as a high concentration of sugar is in contact with the wound surface. If the compositions (a) can be mixed to a substantially uniform consistency shortly before use, (b) can be spread on and will adhere to gauze or similar material, such as a sponge dressing and (c) will stay in place on a wound or burn to which they are applied, they are clearly within the scope of this invention even though they might tend to layer within hours if stored in a receptacle.

Close watch has been maintained to assure the compounding in clean facilities and with clean equipment. A stainless steel mixer and stainless steel blade are recommended. The product is packaged in opaque, dishwasher-cleaned, air-tight plastic containers.

To compound the mixture, e.g., 2 pounds of povidone-iodine solution (10 percent by weight), such as Betadine ® solution, and 5 pounds of povidone-iodine ointment (10 percent by weight), such as Betadine ® ointment, are placed in a 5-gallon stainless steel tub. These are mixed well with a stainless steel blade, powered by a one-half horsepower motor, geared through a reduction gear designed for pizza dough. When the mixture is uniform in consistency, 20 pounds of sugar are added slowly until the mixed batch is of uniform consistency.

The hardware and mixing apparatus are of stainless steel to minimize any contamination of the product by softer metals, such as aluminum. All utensils, including the mixing bowl and blade, the stainless steel spoon and the container jars, are washed with soap and water prior to use.

When the mixture is of uniform consistency (usually after 10 minutes of mixing), the batch is weighed out into clean one-pint plastic containers (jars). These are opaque. Once weighed, the jars are closed tightly and labeled with a batch number, corresponding to the date mixed. This product, thus stored, maintains its consistency over a period in excess of six months.

There are two basic techniques for applying the admixture to wounds. When the wound is deep, the medicine is spread directly onto the wound and then covered with a standard 4×4 (inch) dressing pad or other appropriate dressing material. The subject sugar/povidone-iodine admixture adheres to the wound, making it easy to apply the dressing. The more common technique is to apply this admixture directly onto a 4×4 (inch) pad as if spreading peanut butter on a slice of bread. The pad is then placed over the wound with the medicine-side down. This approach works better when applying dressings to burns and other shallow wounds.

That is to say, the medicine is applied to a wound so as to cover the injured surface completely, generally with one-quarter-inch thickness of the medicine. Dressing-change schedules are dictated by the condition of the wound. In highly-contaminated (pussy) or weeping wounds dressing changes are performed every four to six hours; in other wounds dressing changes are performed less frequently, sometimes only one or two times per day.

Dressings are advantageously changed three to four times a day. Since there seems to be more rapid development of tissue in finger tip amputations, the dressings should be changed somewhat more frequently. With each dressing removal, the residue is easily washed off with tap water or in a whirlpool, if desired. In approximately 50 percent of the cases hydrogen peroxide is useful for cleansing the wound before debridement, and may be necessary as often as once each day in many wounds.

The sugar/povidone-iodine composition tends to enhance wound bleeding when applied to bleeding wounds within twenty-four hours after injury. For this reason, after cleansing or debridement, Iodoform is generally used initially to secure hemostasis in these wounds and the compositon is not applied until the following day or until hemostasis is assured. Once the wound is free of bleeding, the subject admixture is applied as previously described with multiple daily dressing changes.

When epithelialization occurs, a ring of white tissue sometimes appears between advancing skin and granulation tissue. This is usually debrided one to two times a day in order to obtain full skin coverage without allowing an indentation (defect) to occur at the site of the wound.

Repeated daily dressing changes are continued until the wound is healed. Healing time varies, depending upon the type and depth of the wound, but all thus-treated wounds have healed well and relatively quickly.

Sugardyne TM has been useful on a variety of wounds, both infected and non-infected. Infected wounds have been contaminated with *Staphylococcus aureus, E. coli,* and *Pseudomonas aeruginosa,* as well as these in combination, plus numerous other bacterial species. Successfully-treated wounds have included abrasions, older lacerations and shotgun and gunshot wounds involving both small and massive soft tissue injuries and open fractures secondary to these injuries. Other treated injuries have included spider bites involving necrosis; first-, second- and third-degree bruns; frostbite injuries; open fractures to bone; and decubitus, pressure, diabetic and stasis ulcers. The subject composition has not been found successful in treating poison ivy and poison oak unless the patient has excoriated the adjacent skin and it has become infected.

Some success has been experienced on psoriasis; there is a tendency for healing of the psoriatic lesions. On a massive fungating carcinoma of the skin in a 98 year old patient, it caused a rapid decrease in the size of the fungating lesion.

The composition has been proved to be extremely effective in the treatment of a large variety of common and rather uncommon wounds to man where bacterial and fungal contamination ordinarily occur. There has been an extremely high success rate with rapid healing, minimization of hospital in-patient time and burn-unit time, and more rapid patient discharge. There has been a considerable improvement in the end results because of more rapid healing and the elimination of further surgical procedures, including skin grafting.

In those cases where grafting has been required, the donor sites have been treated with the composition. These sites have healed without scarring and became barely perceptible, if at all, as donor sites.

The composition has not only presented itself as an effective healing agent but, because of its anesthetic effects, has significantly reduced the necessity for administering addictive narcotics. Where many patients would normally request a narcotic medication prior to or following dressing changes, these requests have been at a minimum when using the composition. This is particularly true where patients have large open wounds, including painful burns where application of any topical medicine is extremely disagreeable. Therefore, in addition to its wound-healing properties, treatment with the composition has helped to reduce addictive potential for narcotics, especially in patients treated over an extended period of time.

To a large extent thus-treated wounds have healed with no scars or with minimal scarring. The wounded area was left with skin that was normally colored and sensitive, and there has been no recurrence of infections or production of osteomyelitis in any patient treated to date. In many cases antibiotics have been used minimally or not at all in conjunction with this medicine. In many cases the treated wounds have been among the worst seen by the inventor, and they have healed well. Moreover, even with deep wounds, hair has appeared on healed surface tissue. Regardless of bacterial of fungal contamination, the wounds have successfully healed. This was true even where all other employed products failed and where all tried antibiotics were found to be ineffective. This was true using the admixture in an "unsterile" form and applying it without observing "sterile" procedures.

The subject composition (sugar/povidone-iodine admixture) is an effective medicine which has been used and is useful in the treatment of:

1. Abrasions (infected and non-infected)
2. Absesses (boils)
3. Acne (infected and non-infected)
4. Burns (infected and non-infected)
   a. Common burns
      1. First degree
      2. Second degree
      3. Third degree
   b. Other burns
      1. Electrical
      2. Chemical (acid, alkali and others)
      3. Friction (rope and pavement)
      4. Sunburn
5. Carbuncles (closed and draining)
6. Crush injuries—Reduction of tissue edema
7. Debriding agent in tissue necrosis (Brown Recluse spider bites) (infected or non-infected)
8. Deep wounds (infected and non-infected)
9. Erysipelas
10. Exposed bone (infected or non-infected)
11. Felon (only after incision and drainage)
12. Finger tip amputations (large and small) (infected or non-infected)
13. Fracture blisters (infected or non-infected)
14. Frostbite (infected or non-infected)
15. Gangrene (infected or non-infected)
16. Gunshot wounds (infected or non-infected)
17. Lacerations (infected and non-infected)
18. Open wounds to bone (infected and non-infected)
19. Osteomyelitis
20. Paronychia (before and after incision and drainage)
21. Perianal abcesses
22. Pilonidal cysts (infected or non-infected)
23. Post-op dressing (infected or non-infected)
24. Psoriatic lesions
25. Shotgun wounds (infected or non-infected)
26. Stitch abcesses
27. Stump wounds and guillotine amputations (infected or non-infected)
28. Ulcers (infected or non-infected)
   a. Decubitus (bed sores)
   b. Diabetic
   c. Pressure
   d. Stasis (trophic)

To date no attempt at the treatment of eye, ear, nose, throat or genital injuries has been made, and the subject composition has shown no significant effectiveness in the treatment of viral diseases, poison ivy or poison oak. However, it has been effective in the treatment of all wounds, whether contaminated by bacteria, by fungi or by a combination of both. It has been found equally effective against both Gram-positive and Gram-negative bacteria.

The medicine [a substantially homogeneous admixture of from 10 to 80 parts by weight of a suitable sugar (antibacterial tissue nourisher) or sugar-providing component, 1 part by weight of a physically-, pharmacologically- and chemically-compatible antifungal/antibacterial agent which is pharmaceutically acceptable for direct application to tissue of open and deep wounds and at most $33\frac{1}{3}$ percent by weight (based on the total weight of the medicine) of pharmacologically-acceptable (physically-, chemically- and physiologically-) compatible carrier which is sufficient (in amount and in physical properties) to impart to the admixture a consistency which readily enables the admixture to be spread on and to adhere to a sponge or gauze dressing material and to remain in place when applied directly to tissue of an open wound or of a burn] is easily applied. After a wound is cleaned with water or hydrogen peroxide, the medicine is normally applied to a 4×4 (inch) sponge with a tongue blade or knife, and the sponge is then applied to the wound, medicine-side down (directly on the tissue). Alternatively, the medicine is applied directly on the wound and is then covered with a gauze sponge.

The admixture of 20 parts by weight of granulated sugar, 5 parts by weight of Betadine ® ointment and 2 parts by weight of Betadine ® solution (Sugardyne ™) is easily stored. It does not appear to separate over a period of time whether storage is at normal room temperature, in a warm room, or in the refrigerator. Samples have been maintained under each of these conditions for over six months with no separation and no contamination occurring.

There has been no breakdown or reduction in efficacy despite preparation and storage under non-sterile circumstances. Cultures have consistently been negative.

Sugardyne ™ has been applied to most wounds in an unsterile fashion with no deleterious outcome. Each of its ingredients and the final admixture are water soluble and stain neither skin nor clothing permanently. If discoloration does occur, it is easily removed with water and a mild detergent.

Sugardyne ™ is not painful when applied. Most patients have experienced rather rapid relief of pain after its application and, when it is applied to a burn wound, there is almost an anesthetic feeling immediately upon application. A few patients have described a slight sensation of heat after application of Sugardyne ™; rarely do they describe a sensation of pain. The described heat sensation is short-lived, and no patient has reported discomfort to an extent that the use of Sugardyne ™ was discontinued.

Sugardyne ™ tends to prevent the growth of new tissue into the dressing material while allowing full exuberant granulation tissue to grow. This allows dressing changes to be made easily without disturbing the healing wound and without pain to the patient. If it is absorbed, it is metabolized and not excreted. No known data suggest any harm secondary to this absorption. If sucrose is hydrolized by tissue fluids and bacterial enzymes on a wound surface, the absorbed materials would be glucose, fructose and/or their metabolites. Unlike salt (NaCl) these substances are metabolized rather than excreted from the human body. Therefore, in elderly patients with cardiac or renal disease the absorbed products do not present a potential cardiovascular-renal problem. Further, no evidence suggests that the product is diabetagenic, either in the diabetic or non-diabetic patient. No deleterious effects have been observed following the topical administration of povidone-iodine or of the admixture (except for the previously-noted precaution for a bleeding tendency) when applied to fresh, bleeding wounds.

Where comparisons have been available on the same patient, a medicine of this invention has out-performed all other medications commonly used for treating similar wounds. These medications include Silvadene, Iodoform gauze, Xeroform gauze, P-I (povidone-iodine) ointment and P-I solution when used alone.

By comparison, in most burn wounds and wounds where eschar (scab) formation is common, most other products allow the formation of eschar while subject medicines do not. As a result, a very clean, rapidly-granulating wound is achieved within a brief period, usually from one to three days. Although the use of a subject medicine usually reduces any need for grafting, wounds requiring such treatment are potentially able to be grafted sooner. Additionally, most other products require the concomitant use of antibiotics; they have generally not been necessary when using a subject medicine, e.g. Sugardyne TM.

Total hospital time in the Burn Unit is greatly reduced by the use of a subject medicine, since burn wounds are rapidly converted to clean, healing, non-contaminated wounds. Since further contamination has not been a problem, the burn patient can be treated with whirlpool and with multiple dressing changes on the ward rather than in the Burn Unit. Patients are not only released from the Burn Unit sooner; they, like non-burn patients, are released from the hospital more quickly.

Sugardyne TM has been especially helpful in treatment of diabetics for whom amputations would be the normal course of events after the development of a diabetic ulceration of the foot. The medicine, even in the face of a rather large contaminated ulcerative area, including osteomyelitic bone beneath the ulcer, has resulted in rather rapid healing of the diabetic ulceration. There has also been rather rapid healing of the underlying osteomyelitis, despite the fact that, in many cases, systemic antibiotics were not used or were minimally effective according to laboratory testing.

To date there has been a reduction in the total number of amputations performed on diabetics because the early diabetic ulcer, even with underlying osteomyelitis, usually responds quickly to treatment with, e.g., Sugardyne TM. Further, wounds to extremities (especially fingers and toes) in non-diabetics, normally requiring amputation, have been more likely to be viable and salvageable. Skin grafts have been reduced in number since the medicine rapidly tends to fill the defect created by the wound. It leaves clean granulation tissue which subsequently levels off at the level of the normal surrounding soft tissue. It epithelializes with normal, sensitive skin and normal skin color. Scars are minimal, defects are minimal, and the patients are quite happy with the results. Most patients are able to use the product at home without significant difficulty and with a reduced number of follow-up visits, either in the hospital, in physical therapy or in the physician's office.

Most of the wounds treated with a subject composition are wounds which would be expected to heal more slowly, since they heal by secondary intention. Actual results suggest that these wounds heal much more rapidly than similar wounds not so treated; significantly, many heal as rapidly as wounds treated by primary intention.

Wounds heal in a brief period of time with minimal scarring; healed tissue is free of hypertrophic scarring. To date there have been no keloids. Both laymen and physicians agree that the wounds are healed "without scar."

Color and sensation are generally restored to normal. Damaged neural elements are encouraged to grow in such a way as to re-innervate the injured area and to replicate normal sensation.

Wounds in which bone was exposed and infected have responded dramatically to treatment with a subject medicine. Exposed, infected, uncovered and unprotected bone is generally expected to die. Most physicians agree that every possible attempt should be made to cover such exposed bone, even in the face of its infection. Numerous operations have been devised to carry out this objective. These operations include skin grafting, advancing flaps, relief incisions with advancement of tissue over exposed areas, muscle releases and muscle transfers, including the use of abdominal, cross-arm and cross-leg flaps. None of these techniques has had to be employed when exposed bone was present in a wound to which a subject medicine was applied. The medicine has cleaned the wound and the bone, allowing granulation tissue to cover the wounded area and the bone, with eventual complete filling of the defect and complete coverage by skin. No patient treated with this medicine, with or without the use of systemic antibiotics, has developed osteomyelitis. These data should be contrasted with the prevalence of osteomyelitis following open fractures compentently treated by standard techniques and appropriate antibiotic coverage; a three to six percent rate of osteomyelitis is common.

Limited experience has shown that a subject medicine, applied to fresh first- and second-degree burns, provides immediate relief of pain and rapid healing of the injured area. Where blisters are present, they either rapidly resolve or are protected to allow normal healing to progress beneath them at a more rapid pace. Therefore, in conditions where blisters and potential infection are otherwise problems (such as fracture blisters or crush injuries), a subject medicine has been effectively used to induce rapid healing. In patients having third-degree (full thickness) burns and treated with the subject medicine, rapid conversion of damaged tissue to clean, graftable granulation tissue usually occurs in from three to four days.

One patient (not an adolescent) had acne on his back, and this condition rapidly healed in response to treatment with Sugardyne TM. This product has produced dramatic results in those patients where stitch abscesses (very similar to acne) have been treated following surgery. They are usually healed completely in one to two days, and there is good reason to believe that a similar response would be found in adolescents with acne.

In the face of ever-escalating costs for medical treatment and hospital care, the subject compositions represent medicines which not only produce results in healing never before demonstrated, but which are safely used on a wide variety of wounds by the patient at home with minimal direct supervision by a physician. Their components are readily available and inexpensive. The restrictions on their use are minimal and the advantages found in their use far outweigh the few disadvantages.

EXAMPLES

Suitable ointment base is prepared by heating polyethylene glycol 4000 (400 grams) and polyethylene glycol 400 (600 grams) on a water bath to 65° C. After cooling, this ointment base serves as an appropriate carrier, adding water, wetting agents, or detergents, as necessary, to achieve a desired consistency. For example, modification of the formulation yields 234 grams of carrier (A) referred to in later formulations.

Representative examples of 1000-gram formulations are:

(1) Bismuth tribromophenate—30 grams, soft paraffin—300 grams, sugar—670 grams.

(2) Triiodomethane—30 grams, soft paraffin—350 grams, sugar—620 grams.

(3) Zinc oxide—200 grams, carboxymethyl cellulose—7 grams, water—63 grams, honey—730 grams.

(4) Gentian violet—13 grams, carrier (A)—234 grams, fructose—376 grams, glucose—377 grams.

(5) Resorcinol—50 grams, soft paraffin—250 grams, sugar—700 grams.

(6) Honey—100 grams, povidone iodine—10 grams, carrier (A)—234 grams, sugar—656 grams.

(7) Ichthammol Ointment—350 grams, sugar—650 grams.

Base IV (consisting of polyethylene glycol 4000—425 grams, polyethylene glycol 400—375 grams, and 1,2,6-hexanetriol—200 grams) his the carrier for Examples 8 to 10.

(8) Sugar—730 grams, amphotericin B—30 grams, and base IV—240 grams.

(9) Hexachlorophene—30 grams, sugar—730 grams, and base IV—240 grams.

(10) Zinc undecylinate—200 grams, sugar—550 grams, base IV—250 grams.

Substantially homogeneous compositions are prepared from sugar (S), PVP-I (I) and carrier (A) as follows:

| Carrier Ingredients | Parts by Weight |
|---|---|
| Polyethylene glycol (PEG) 400 | 111.11 |
| PEG 4000 | 45.29 |
| Sodium phosphate (tribasic) | 0.55 |
| Triton X-114 (octylphenoxy polyethoxyethanol) - wetting agent | 0.29 |
| Water | 76.55 |

| | Weight Ratio (S)/(I) | (A), parts by weight | (I), parts by weight | (S), parts by weight |
|---|---|---|---|---|
| (11) | 30/1 | 234 | 24.71 | 741.3 |
| (12) | 35/1 | 234 | 21.28 | 744.8 |
| (13) | 40/1 | 234 | 18.68 | 747.2 |
| (14) | 45/1 | 234 | 16.65 | 749.25 |
| (15) | 50/1 | 234 | 15.02 | 751 |
| (16) | 60/1 | 234 | 12.56 | 753.6 |
| (17) | 70/1 | 234 | 10.79 | 755.3 |
| (18) | 80/1 | 234 | 9.46 | 756.8 |
| (19) | 10/1 | 222.97 | 70.82 | 708.22 |
| (20) | 15/1 | 226.30 | 48.36 | 725.33 |
| (21) | 20/1 | 229.07 | 36.31 | 734.21 |
| (22) | 25/1 | 230.77 | 29.59 | 739.65 |
| (23) | 30/1 | 231.92 | 24.78 | 743.33 |
| (24) | 35/1 | 232.74 | 21.30 | 745.95 |
| (25) | 40/1 | 233.37 | 18.70 | 747.98 |
| (26) | 45/1 | 233.86 | 16.65 | 749.55 |
| (27) | 50/1 | 234.23 | 15.02 | 750.75 |
| (28) | 60/1 | 234.82 | 12.54 | 752.63 |
| (29) | 70/1 | 235.24 | 10.77 | 753.98 |
| (30) | 80/1 | 235.57 | 9.43 | 755.03 |

In the preceding compositions (S), which is sucrose, is optionally replaced by other antibacterial tissue nourishers, such as:

| | | | |
|---|---|---|---|
| aloe | pine pitch | honey | glucose |
| kerosene | tar oil | molasses | dextrose |
| urea | maple syrup | sucrose | maltose |
| pine oil | sorghum | fructose | invert sugar |
| brown sugar | | | | with corresponding changes in the consistency of the carrier. Honey is optionally used as a carrier ingredient.

The PVP-I is optionally replaced (wholly or partially) by other antifungal/antibacterial agents, such as other iodophors ("tamed iodines", e.g. poloxamer-iodine complex), phenol, iodine tincture, bismuth tribromophenate, iodoform, and a combination of bismuth tribromophenate with iodoform.

CASE HISTORIES

In the following cases Sugardyne TM is employed as the medication in the absence of a specific statement to the contrary.

The typical dressing technique with this medication involves removing any prior dressing, cleansing the wound with soap and water and then with hydrogen peroxide, applying Sugardyne TM directly to the wound with a tongue blade, completely covering or filling the wound. Alternatively, the Sugardyne TM is applied to a 4-inch×4-inch sponge and the thus-obtained dressing is applied, face down, to the wound. Dressings are changed two or three times daily, adjusting the frequency of dressing changes and Sugardyne TM application to the type and severity of the wound. More serious wounds are changed more frequently, based on clinical judgment and experience. These techniques are employed in the following case histories unless otherwise indicated.

I. AW is a 22-year old black male who was treated for a neuroma involving the left great toe, with subsequent removal of the great toenail to excise the neuroma. The nail bed was initially treated with Iodoform. This was followed by treatment with the medication (Sugardyne TM ) without any use of antibiotics, to effect a clean-healing nail bed. Sugardyne TM dressings were thereafter changed twice a day for three days. AW was able to use the medication without pain and was able to return to work three days following the surgical procedure.

Commentary: This case demonstrates the ease of application of the medication and the lack of pain while using the medication on an out-patient basis. It also shows the capacity of the patient to return to work quickly and during the healing process.

II. A 70-year-old white female (RA) was treated for infection secondary to the previous operation for an ankle fracture. The patient had a draining wound on the medial aspect of her leg in the area of the previous surgery. She had been an antibiotics for a considerable period of time in view of an open fracture. She was placed on daily Sugardyne TM dressings, with dressing changes (after cleaning the wound with hydrogen peroxide) twice daily, and Keflex (500 mg) every six hours. The wound was nearly completely healed (with no signs of infection) within seven days following initial treatment. Her course was painless.

Comment: With the use of Sugardyne TM, the course of treatment was painless, the resultant healing was rapid and the application was easy.

III. A 12-year-old white female (BB) was treated with Sugardyne TM for tape burns following a hip operation. Painless dressing changes were effected twice a day for three days, after which time the injured skin was healed without antibiotics and without leaving a scar.

IV. A 90-year-old white male (JD) was treated for multiple fractures of the left foot. He was treated with a closed reduction, and some three weeks later he appeared to be doing well. When his cast was removed, he had a mild leg and foot edema. He subsequently developed tremendous edema secondary to disuse and his age, and three days after cast removal he was noted to have erythema and a weeping infected area involving much of his foot, ankle and leg secondary to self-induced scratching. The subject tissue was cleansed with Betadine solution and was thereafter treated with Sugardyne TM over the wounds. Prior to dressing with Sugardyne TM (two times each day), the involved tissue was washed with hydrogen peroxide. Although he was directed to take Keflex (500 mg) every six hours, he subsequently stated that he did not take this antibiotic. One day after his initial treatment with the medication much of the erythema and superficial infection had cleared. Three days later his infection was substantially healed, and by six days he had nearly complete healing. He went on to complete healing without scars.

Comment: This case demonstrates the effectiveness of the medication in an elderly patient with edema and erysipelas, without concomitant use of antibiotics.

V. A 23-year-old white male (NE) sustained a massive gun-shot (0.357 caliber Magnum) wound to the left hand on Sept. 26th, 1978, with loss of bone and soft tissue surrounding and distal to the distal half of the third metacarpal and the proximal half of the proximal phalanx of the long finger, including the MP joint. He was initially treated with Iodoform packing to the open wound and was subsequently treated with whirlpool, hydrogen peroxide and dressing changes with Sugardyne TM. Thereafter, he underwent revision of the wound of the hand and amputation of the long finger. He was discharged eight days after the original injury. The wounds on the palmar and dorsal surface of the hands were nearly completely closed two and a half weeks after injury, with no sign of infection. At four and a half weeks after injury he had full functional use of the remaining fingers of the hand and was able to make a good strong fist.

Commentary: This case demonstrates the effective use of the medication in a massive gunshot wound involving the hand with subsequent minimal scarring and rapid healing, with rapid return to work and full function.

VI. A 6-year-old black male (HF) had apparently fallen from his bicycle and injured his left knee three days prior to being seen in the emergency room. He was running a temperature in excess of 102° and had been given penicillin, but, when first examined, an infected abrasion with erythema was noted in and around the surface of the left knee. The patient was treated in the emergency room using Sugardyne TM and continued on penicillin. One day later he had clean-healing wounds with marked reduction in the size of the wound. The wounds had nearly completely healed (with no signs of infection and minimal scarring) within six days thereafter.

Commentary: This patient demonstrates rapid healing of a serious wound, continuing the use of an antibiotic which had previously been ineffective. He was treated without pain and with no scarring; he was able to be treated without hospitalization.

VII. A 28-year-old black female (BMB) was treated for an infected burn on the back of her hand with Sugardyne TM. The dressing was changed twice a day. Healing was effected without a scar in less than one week.

VIII. A 36-year-old black male (DC) sustained a deep laceration of his right index finger when an engine block fell on his hand. Initial treatment included suturing of the wound. This was followed by daily dressing changes with Sugardyne TM. Substantial healing was effected in nine days with such treatment. A full range of motion was obtained in sixteen days, with no scarring.

IX. A 49-year-old white female (IN) was involved in a motor vehicle accident in which she sustained a large hematoma (blood collection) on her left calf. This was drained in the Emergency Room and packed with Iodoform. Subsequently, daily dressing changes with Sugardyne TM produced a non-scarred, healed wound in two weeks.

X. A 34-year-old white male (LP) had been treated for an ulceration and multiple small abscesses involving nearly the entire distal end of a left, below-knee, amputation stump with a number of medications, including topical creams, ointments, poultices, antibiotics and steroids for approximately a year, all to no avail. On examination, the patient exhibited a very large ulcer with small abscesses involving the entire 3-inch × 3-inch diameter below-knee amputation stump on the weight-bearing surface. The patient appeared to have both fungal and bacterial contaminants. He was first treated with Sugardyne TM without concomitant use of antibiotics on Oct. 31, 1978, and two weeks later he had approximately $\frac{3}{4}$ closure of the distal-stump wound with minimal amounts of drainage. The Sugardyne TM dressing was changed three times each day after cleansing the wound (each time) with soap, water and hydrogen peroxide. The wound had nearly completely healed within one month, despite the fact that the patient continued to work during the entire course of treatment.

Comment: This massively-ulcerated wound, unresponsive to a number of other acceptable treatments, responded rapidly and without hospitalization to Sugardyne TM without interruption of a work schedule. The patient had no complaints of pain during the use of this medication; he found it easy to use and easy to apply.

XI. A 5-year-old white male (RC) was injured when his right foot was caught in a log splitter. He sustained necrosis to the skin on the lateral aspect of his foot and a massive crush injury to the entire foot, resulting in tremendous swelling and loss of normal blood supply distally. He subsequently underwent a fasciotomy to the foot and was treated with whirlpool and Sugardyne TM to his wounds after packing with Iodoform for two days. When the Iodoform packing was removed, the wound was free from blood. The patient made excellent progress, and the wound had nearly completely healed by the end of three weeks. By 27 days the patient had complete healing with minimal scarring both medially and laterally. He had complete filling in of the medial defect and complete restoration of the lateral area which had previously been necrotic. There was normal sensation, normal color, minimal scarring and full range of motion and function.

Comment: Expected healing time was markedly reduced without any necessity for a skin graft. The patient had no complaints of pain during application of the Sugardyne ™.

XII. A 16-year-old white male (TS) sustained a finger-tip amputation on Dec. 25, 1978. Initial treatment was with an Iodoform dressing. On the second day following the amputation the Iodoform dressing was removed and the wound was dressed with Sugardyne ™. Dressing changes were made three times each day. By the fourth day the patient had a clean-healing wound with good granulation tissue in the wound. On the eight day the patient had excellent progression of healing with a small indentation in the center of the wound; he was continued on Sugardyne ™ dressing changes three times a day with intermittent cleansing with hydrogen peroxide. The wound was nearly completely healed six days later and, by Jan. 11, 1979, the wound was completely healed. The patient had normal sensation and normal color with a very slight defect in the fingertip in terms of total length.

Commentary: Treatment using Sugardyne ™ resulted in restoration of finger length, alleviated need for a skin graft, avoided antibiotics and resulted in a rapidly-healing wound. Moreover, the total expense of treatment was markedly less than would be expected with other medicaments.

XIII. A 7-year-old white male (DP) was treated following a crushing injury (to the tip of his right index finger) sustained in a motorcycle accident. He had been treated for from 10 to 12 days prior to this time and was noted to have a massive infection involving the entire end of his finger, from the last joint to the tip. He was treated with Sugardyne ™, using three to four dressing changes per day (cleansing the wound each time with hydrogen peroxide). Nearly complete healing was effected within one week; complete healing was accomplished in 13 days without any scarring.

XIV. A 61-year-old black male (GK) was treated for injuries to his left hand. He had sustained crush injuries and deep lacerations (including tendons) of the index, long and ring fingers. He was initially treated with Iodoform; this was followed by whirlpool and application of Sugardyne ™. Dressing changes were effected twice a day with hydrogen peroxide. Nearly complete healing ensued with minimal scarring. A full passive range of motion was restored within four weeks. Complete healing of the long- and ring-finger injuries was accomplished in less than two weeks.

XV. A 5-year-old white male (RH) apparently fell and suffered multiple abrasions of the right hand, the right side of his face and forehead. He was seen one day later, having an elevated temperature, and his wounds were covered with pus. After cleansing, his wounds were dressed with Sugardyne ™. His mother changed his dressings twice a day, and the patient was placed on erythromycin (250 mg) every six hours. Two days later the patient's wounds were without signs of infection and were nearly completely healed. There were no signs of scars.

Comment: The healing was rapid. The patient did not complain of any pain during the course of dressing changes.

XVI. A 41-year-old white male (RK) sustained a deep abrasion to the right shin at its midpoint, down to the bone. This wound was infected with Mississipi River mud and water. Within two days it was highly contaminated and infected. Treatment was initiated on the second day with Sugardyne ™ dressings, changed twice daily after cleansing (each time) with hydrogen peroxide. The wound proceeded to heal rapidly without further infection and was covered with skin with a slight brownish discoloration, but which had full sensation and full hair covering.

Commentary: This case demonstrates the effectiveness of Sugardyne ™ on wounds with open exposed infected bone and soft tissues and without concomitant use of antibiotics, resulting in rapid and painless healing.

XVII. A 41-year-old white male surgeon (RK), who sustained first and second degree burns to his left hand after a match book exploded in his hand, resulting in burns on the volar and dorsal aspects involving the base of the thumb, the palm, dorsum of the hand and all four fingers. Immediate treatment consisted of application of Sugardyne ™ and a dry dressing. The patient was subsequently able to remove the dressing in four hours with complete resolution of the first and second degree burns, including all but two small blisters. Pain relief was immediate, and the patient was able to return to a full schedule of duties, including full use of the hand, in four hours. He was able to operate the next morning with no evidence of burns and no pain.

Comment: This case demonstrates the effectiveness both in terms of rapid healing and in terms of pain relief in the burned patient. It demonstrates the capacity of Sugardyne ™ to allow a patient to return to full working capacity quickly and without pain.

XVIII. A 63-year-old white male (AK) sustained a gunshot wound in 1965 to his right ankle, with subsequent fusion of the ankle. The patient has intermittently had purulent drainage from the ankle and such drainage has generally cultured *Staphylococcus aureus*. He has generally had to be on antibiotics because of the drainage, which ordinarily healed after a period of swelling and drainage. The patient has been treated with Sugardyne ™ since June 1978, and has had a reduction in the number of flare-ups. He has also had rapid healing with using Sugardyne ™ when a flare-up occurred. He generally begins Sugardyne ™ treatment as soon as he sees any erythematous area; healing usually follows within one or two days.

Commentary: This patient demonstrates the effectiveness of Sugardyne ™ in chronic osteomyelitis and also shows the effectiveness of this medicament when compared with this patient's usual response to antibiotics alone.

XIX. A 22-year-old white female (EH) was treated in the Emergency Room after an automobile accident on Aug. 5, 1978, in which she sustained multiple abrasions and lacerations and a deep laceration to the medial aspect of her left knee. After cleansing, the deep lacerations of the knee were closed over a drain, and the patient was dressed with Sugardyne ™. Two days thereafter her wound was healing well without signs of infection. By the sixth day her wounds were nearly completely healed. Her wounds subsequently healed with minimal signs of scarring in all abrasion and laceration sites, and she had no keloid formation. Dressings were changed twice a day during treatment.

Commentary: This patient was able to be treated without antibiotics and made an uneventful, unscarred, comfortable recovery using Sugardyne ™.

XX. A 13-year-old white male (JW) suffered a laceration and fracture to his left elbow one week prior to treatment in the Emergency Room. He had an erythematous area on the lateral aspect of the elbow and was febrile. He appeared to have an early infected laceration of the left elbow. Treatment included cleansing with Bedatine® scrub and dressing with Sugardyne TM. The patient was placed on Keflex (250 mg) every six hours. On the following day the patient's symptomatology had diminished considerably, and much of the erythema was gone. Within two days thereafter the early infection had completely healed.

Comment: This case demonstrates rapid healing of an infected laceration and open fracture by use of Sugardyne TM used concomitantly with antibiotics.

XXI. A 35-year-old black male (CW) was admitted to the hospital after having been stabbed through and through the mid portion of the left arm at the level of the bone. The patient's initial treatment consisted of intravenous antibiotics and open packing of the wound to prevent infection. He was subsequently treated with Sugardyne TM in the hospital and on an out-patient basis until the wound was clean enough to be closed with sutures. This was done three weeks later, and he went on to an uneventful recovery without further infection.

Comment: The potential for infection in this serious wound was alleviated by the use of Sugardyne TM and antibiotics. The patient healed with minimal scarring and no infection. Much of his treatment was accomplished on an out-patient basis.

XXII. A 54-year-old white female (KW) was treated for a massive infection of her left leg. The infection subsequently resulted in a massive abscess, requiring an open amputation on June 5, 1978. Because of the slow resolution of her infection, she was treated with Sugardyne TM as well as antibiotics, and this resulted in complete cleaning and granulation of the distal stump. Subsequently, she underwent a revision of this amputation and was able to be discharged from the hospital six days later. By the end of three weeks the stump was completely healed, with no signs of even a linear scar. She was subsequently fitted with a below-knee prosthesis and has had minimal problems since that time. The Sugardyne TM treatment involved dressing changes three times each day. Antibiotics were administered every six hours during treatment.

Commentary: A difficult problem in a middleaged diabetic was handled successfully using Sugardyne TM with rapid healing, so that a second procedure could be done to enable the patient to be discharged from the hospital sooner. Her course was markedly improved using this medicament, and the potential for death following an infection of this type was avoided with the concomitant use of Sugardyne TM and antibiotics. No progress was made prior to treatment with Sugardyne TM.

XXIII. A 54-year-old white female (MW) developed stitch abscesses following surgery on her wrist. She was treated with Sugardyne TM and with Keflex (250 mg) every six hours. She subsequently proceeded to heal well with no sign of a scar.

Comment: This case demonstrates the use of Sugardyne TM for a commonly-encountered problem following surgery.

XXIV. A 35-year-old black male (JK) was injured on May 28, 1978, while riding his motorcycle. He suffered multiple abrasions of both upper extremities, including the shoulders, outer surfaces of the arms and forearms, including the hand and knuckles (especially on the right side).

The wounds were initially treated in the Emergency Room. After one day they were covered with large amounts of pus and appeared to be nearly burned. The wounds were cleansed with Betadine® solution and were redressed with Sugardyne TM. Within two days the wounds were clean; there was fresh granulation tissue and no sign of infection. The wounds were nearly completely filled within one week, and most were completely skinned over with normal negroid skin. Three days later his wounds were nearly fully healed, and he had brown skin covering all previously-injured tissue. The tissue was normal in sensation.

Commentary: The patient was able to treat his wounds at home without infection and with a good end result in what could very well have become a serious burn-like systemic infection. His wounds healed with Sugardyne TM with no scarring and no depigmentation. His treatment was without pain.

XXV. A 26-year-old white male (JMC) had sustained a dirty laceration of the mid portion of the volar aspect of his right forearm, which subsequently became infected (despite antibiotics) some five days following initial treatment. The initial treatment included removal of a few sutures and packing of the wound with Iodoform. Two days thereafter the wound, which was purulent, but had no bleeding, was treated with Sugardyne TM. It subsequently healed without further infection and with minimal scarring in approximately 7 days. The patient dressed his wounds on a daily basis, using hydrogen peroxide to wash the wound, Sugardyne TM and a dry dressing.

Commentary: The patient was able to continue work despite this infected wound and was able to heal rapidly without pain secondary to his injury.

XXVI. A 58-year-old white male (WMG) had undergone a partial amputation of his right foot secondary to diabetic gangrene approximately 10 years prior to being seen. He had had ulcerations of the foot, requiring multiple hospitalizations on nearly a monthly basis for approximately two or three years. During that period of time the patient had become addicted to medications for pain. He had been treated with a large variety of the usual medications, both systemic and oral antibiotics, as well as wound dresssing materials, to treat his ulcer. As a general rule, when his ulcer became badly infected, his diabetes went out of control, and the patient was forced to be hospitalized. During the course of almost a year the patient has been using Sugardyne TM for daily dressing changes, washing his wound with soap and water and hydrogen peroxide prior to each such change. During this period he had not required hospitalization, nor has he required continuous antibiotics as he had in the past. His diabetes has been stable, and he has been free of any pain, thereby freeing him of his need for narcotics.

Commentary: Although this patient's diabetes and chronic ulcerations of the foot have not healed, he has been stabilized to the point where repeated hospitalizations have not been necessary, and his diabetes has been well controlled with the use of Sugardyne TM for basic chronic wound care. He is now cured of his previous narcotic addiction.

XXVII. A 29-year-old white male (CMD) was injured three or four days prior to being seen. A large plank fell across his ankle, inflicting soft-tissue injury as well as a significant sprain. The patient subsequently developed an abscess which was drained and treated with Sugardyne TM. The initial treatment included packing with Iodoform dressing, which was removed after one and a half days, at which time there was some purulence, but no bleeding. Within four days after the initial treatment the wound was nearly completely healed.

Comment: The patient was able to be treated on an out-patient basis for a rather significant injury to his ankle, the injury did not require use of concomitant antibiotics. The patient was able to use Sugardyne TM with ease and without pain.

XXVIII. A 10-year-old black male (PD) sustained a deep laceration and contusion to the distal portion of the right index finger, including a fracture of the tuft, when a brick fell on it. The patient's initial treatment was with Sugardyne TM. The patient underwent one Emgergency-Room dressing change and wound check. Within four days the wound was completely healed with no signs of scarring.

Commentary: This case demonstrates rapid uneventful healing with minimal hospitalization time, no antibiotics, ease of application and minimal pain for the patient.

XXIX. A 30-year-old white female (SH) was treated in the Emergency Room after having suffered an axe injury with an open fracture of the middle phalanx of the left long finger. She was treated primarily with open reduction, internal fixation and suturing of the lacerated extensor tendon, placed on antibiotics and Sugardyne TM dressing changes after suturing of the skin wound. She healed rapidly without infection. She subsequently had minimal visible scar of the finger with no keloid formation. Three months after injury the fracture was completely healed.

Commentary: A seriously-injured, nearly amputated finger was capable of treatment without hospitalization of the patient; it healed with Sugardyne TM treatment without scarring. The patient was able to treat herself at home with minimal discomfort.

XXX. A 7-year-old white male (JL) suffered near amputations (by an axe) of his index and long fingers of his left hand. The patient underwent initial cleansing and stabilization of fingers with K-wires. He had repair of extensor tendons and closure of skin, dressing wounds with Sugardyne TM. The patient made an uneventful recovery, with nearly complete healing of wounds within one week. There was no infection. Subsequently, open fractures healed without incident. The patient had no visible scars.

Comment: Case illustrates rapid healing of contaminated injured tissue, including bone, without infection with Sugardyne TM as the primary wound dressing agent.

XXXI. A 59-year-old meat cutter (HB) who amputated the distal one-third of his right long finger (distal phalanx) while working as a butcher, received initial treatment in the Emergency Room. This treatment involved stopping the bleeding from the soft tissue and bone in the end of the amputated tip. Treatment was with Iodoform gauze, followed in one day with Sugardyne TM. Subsequent dressing changes were twice daily, with hydrogen peroxide cleansing preceding each. The patient proceeded to complete healing in four weeks, with regeneration of approximately three-fourths of the lost tissue, with no skin graft. He had good feeling and excellent pulp overlying the fingertip.

Comment: This case illustrated regeneration of tissue following fingertip amputation, utilizing Sugardyne TM for daily dressing changes. No antibiotics were used despite open exposed bone. The treatment was substantially painless.

XXXII. A 10-year-old white male (JW) was treated for a two-inch sliver embedded in the sole of his right foot. After cleansing the foot, the sliver was removed under local anesthesia. Sugardyne TM was used to dress the wound, and the patient was placed on antibiotics by mouth. The foot healed completely in two days without infection and with dressing changes twice a day.

Comment: This case demonstrates the effect of Sugardyne TM on contaminated tissue, both in terms of preventing infection and of rapid healing. The oral antibiotic was Keflex, which was administered every six hours during treatment.

XXXIII. A 16-year-old white male (WM) had been injured 19 days prior to being seen; the fourth and fifth fingers of his left hand had been sprayed with liquid propane, resulting in a frostbite injury (full thickness-third degree), especially to the mid-dorsal portion of his fifth finger. Both fingers were initially badly blistered and, despite treatment elsewhere with Betadine ® (P-I) solution, both fingers had become infected. Nearly two-thirds of the dorsum of the fifth finger was infected over both the PIP and DIP joints. On Jan. 4, 1979, nineteen days after injury, the patient was started on Sugardyne TM dressings two to three times each day. Within four days thereafter the wound was clean, with no signs of infection. On the fourth day a $\frac{1}{8}$-inch border of skin had appeared at the wound edges; 11 days later the wound was more than 50 percent covered with skin. Two weeks later the wound was completely healed, with no evidence of scar. The patient had obtained a full range of motion of all finger joints.

Comment: This case demonstrates the effectiveness of Sugardyne TM on a difficult burn-type wound, overlying joint creases. Rapid healing, despite previous treatment with P-I solution alone, which had been ineffective for three weeks.

XXXIV. A 15-year-old white male (KB) suffered an open fracture of his right tibia, with bone protruding through the skin, while riding a motorcycle on July 24, 1978. Irrigation and debridement was carried out in an operating room; stabilization was obtained with K-wires and a cast. The wound was approximated (closed) over a drain and was subsequently treated with Sugardyne TM three times a day, with physical therapy twice daily. Within 16 days the wound had completely healed with no infection. The patient had been on antibiotics, i.v. and orally, for seven days. The recovery was uneventful with no osteomyelitis.

Comment: This case illustrates an open fracture which was successfully treated with Sugardyne TM, with no wound or bone infection and no tissue scarring.

XXXV. A 15-year-old white male (TM) suffered open contaminated fracture of his right tibia. He was treated in an operating room with irrigation and debridement of the open wound, with closure loosely over a drain. The fracture was stabilized using K-wires and a cast. Further treatment included removal of the drain and i.v. antibiotics. Sugardyne TM was started on the third day, with resultant healing without infection. The bone healed in usual fashion without infection.

Comment: This case demonstrates effectiveness of Sugardyne TM in open fractures. There was normal rapid healing of the wound and fracture without infection, and there was no scar.

XXXVI. A 13-year-old black male (VW) was treated for a large abscess of his left knee. He had sustained an injury to the knee some three weeks earlier in a fall. The injured area developed a hematoma which developed a 3-inch×4-inch abscess. The abscess was drained under local anesthesia on Feb. 27, 1979. Large amounts of pus were drained from the abscess, which was packed with Iodoform, and dressed with Sugardyne ™. The patient was seen for repacking in the Emergency Room each day over the weekend, and nearly complete resolution of the abscess was effected in four days. Nearly complete healing had occurred in six days. The patient made complete recovery with no recurrence of the abscess.

Comment: This case illustrates usefulness of Sugardyne ™ to help draw pus from a wound or abscess. It also shows the use of this medicament in the complete rapid healing of a wound.

The invention and its advantages are readily understood from the preceding description. Various changes may be made in the process and in the compositions without departing from the spirit or scope of the invention or sacrificing its material advantages. The process and compositions hereinbefore described are merely illustrative of preferred embodiments of the invention.

What is claimed is:

1. A storage-stable, spreadable, adherent, cohesive substantially-homogeneous therapeutically-acceptable antimicrobial ointment or salve which is an admixture comprising 20 parts by weight of ordinary granulated sugar, 5 parts by weight of Betadine ® ointment and 2 parts by weight of Betadine ® solution.

* * * * *